United States Patent
Huang et al.

(10) Patent No.: US 11,213,413 B2
(45) Date of Patent: Jan. 4, 2022

(54) STENT

(71) Applicant: SHANGHAI MICROPORT MEDICAL (GROUP) CO., LTD., Shanghai (CN)

(72) Inventors: Chubo Huang, Shanghai (CN); Zhilong Li, Shanghai (CN); Bin Xia, Shanghai (CN); Wei Liu, Shanghai (CN); Hao Tian, Shanghai (CN); Qiyi Luo, Shanghai (CN)

(73) Assignee: SHANGHAI MICROPORT MEDICAL (GROUP) CO., LTD., Shanghai (CN)

( * ) Notice: Subject to any disclaimer, the term of this patent is extended or adjusted under 35 U.S.C. 154(b) by 97 days.

(21) Appl. No.: 16/487,384

(22) PCT Filed: Feb. 12, 2018

(86) PCT No.: PCT/CN2018/076427
§ 371 (c)(1),
(2) Date: Aug. 20, 2019

(87) PCT Pub. No.: WO2018/153300
PCT Pub. Date: Aug. 30, 2018

(65) Prior Publication Data
US 2020/0060850 A1    Feb. 27, 2020

(30) Foreign Application Priority Data
Feb. 21, 2017    (CN) .......................... 201710093918.9

(51) Int. Cl.
*A61F 2/86*    (2013.01)

(52) U.S. Cl.
CPC .......... *A61F 2/86* (2013.01); *A61F 2230/001* (2013.01); *A61F 2230/0006* (2013.01); *A61F 2230/0008* (2013.01); *A61F 2250/0098* (2013.01)

(58) Field of Classification Search
CPC ...... A61F 2/82; A61F 2/86; A61F 2/89; A61F 2/915; A61F 2250/0098
See application file for complete search history.

(56) References Cited

U.S. PATENT DOCUMENTS

| | | |
|---|---|---|
| 6,334,871 B1 | 1/2002 | Dor et al. |
| 2002/0103528 A1 | 8/2002 | Schaldach et al. |

(Continued)

FOREIGN PATENT DOCUMENTS

| | | |
|---|---|---|
| CN | 202027751 U | 11/2011 |
| CN | 202184823 U | 4/2012 |

(Continued)

OTHER PUBLICATIONS

English Translation for CN 203841857 (original presented in IDS dated Aug. 20, 2019) (Year: 2014).*

*Primary Examiner* — Dinah Baria
(74) *Attorney, Agent, or Firm* — Muncy, Geissler, Olds & Lowe, P.C.

(57) ABSTRACT

A stent is disclosed, which includes a stent body (2) and a single-radiopaque component (1) disposed at one or each of a proximal end and a distal end of the stent body (2). The stent body (2) is composed of rings and struts, and one part of the single-radiopaque component (1) is received in a receptacle (3) of the stent body (2) and another part of the single-radiopaque component (1) protrudes out of a surface of the stent body (2). The area of the protruding part (11) of the single-radiopaque component (1) is larger than an area of the embedded part (10), the presence of the protruding part (11) allowing the single-radiopaque component (1) to appear (Continued)

wider and thicker in a radiologic image, enhancing the radiopacity of the stent during surgery.

3 Claims, 10 Drawing Sheets

(56) References Cited

U.S. PATENT DOCUMENTS

| | | |
|---|---|---|
| 2013/0178925 A1 | 7/2013 | Sugimoto et al. |
| 2015/0018934 A1 | 1/2015 | Pacetti |
| 2016/0361182 A1 | 12/2016 | Lumauig et al. |

FOREIGN PATENT DOCUMENTS

| | | |
|---|---|---|
| CN | 102429750 A | 5/2012 |
| CN | 102451051 A | 5/2012 |
| CN | 203841857 U | 9/2014 |
| JP | 2014-138854 A | 7/2014 |
| WO | WO2008137821 A1 | 11/2008 |
| WO | WO-2011-081068 A1 | 7/2011 |
| WO | WO 2013045000 A1 | 4/2013 |

* cited by examiner

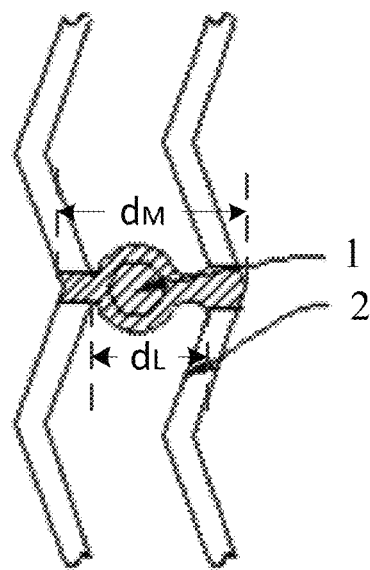
Fig. 13
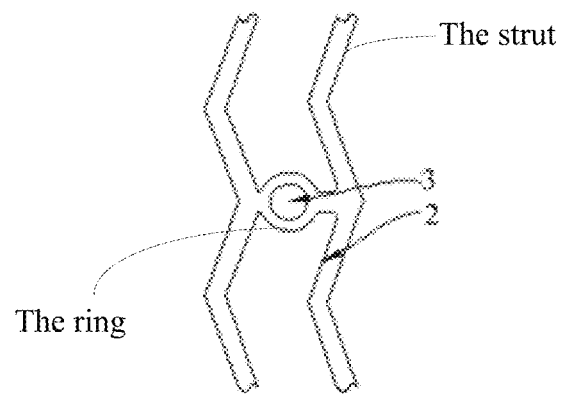
Fig. 14
| Radiopaque markers | Radiologic image obtained at 15 fps in a cinema mode | Display image obtained at 15 fps in a cinema mode |
|---|---|---|
| T-like shape (375 μm) | | |
| T-like shape (410 μm) | | |
| Similar Product | | |
Fig. 15

STENT

TECHNICAL FIELD

The invention relates to the field of medical devices and, in particular, to stents.

BACKGROUND

A bioabsorbable stent, consisting of a polymer stent, a drug coating and an expandable balloon delivery system, is suitable for use in treating an ischemic heart disease caused by a primary coronary artery dissection and improving the coronary artery diameter.

The polymer stent differs from a metal stent in that, in many therapeutic applications, it is expected to stay in the body only for a limited period of time until its intended function is accomplished. Limited by the prepared material, the polymer stent, however, is inferior in radiopacity, when compared to a metal stent. Therefore, in order to enable the physician to know the position of the polymer stent during the procedure in which the stent is employed, it is necessary for the stent to have radiopaque markers for enabling the stent to be radiographically visible.

Currently, one or more radiopaque markers, usually assuming a cylindrical or spherical shape, are typically disposed in struts on both ends of a stent. For example, Chinese Design Patent No. CN302301122S discloses a design with a single radiopaque marker incorporated in a strut. However, due to a limited space of the stent for accommodating the radiopaque marker, the radiopaque marker is made with a limited diameter and thickness and may place a limitation upon the stent in a contracted configuration. In order to achieve increased radiopacity of the stent, WO2008137821A1 discloses a design with two radiopaque markers incorporated in a strut, which are spaced apart along a centerline of the strut. This design, however, requires an adequate length of the strut to carry the radiopaque markers, which may lead to degradations in some stent properties.

Therefore, there is still a need in the art for a solution ensuring both satisfactory radiopacity and performance of a stent.

SUMMARY OF THE INVENTION

It is an objective of the present invention to provide stents, which can overcome the problem of unsatisfactory radiopacity of conventional stents.

To this end, the present invention provides a stent, including a stent body and a single-radiopaque component disposed at one or each of a proximal end and a distal end of the stent body, the stent body composed of rings and struts, the single-radiopaque component having an embedded part received in a receptacle of the stent body and a protruding part protruding out of a surface of the stent body, an area of the protruding part of the single-radiopaque component being larger than an area of the embedded part.

Optionally, in the stent, the protruding part may include an upper surface and a lower surface, the upper surface forming an angle of greater than 90 degrees or smaller than 90 degrees with respect to an axis of the single-radiopaque component.

Optionally, in the stent, a peripheral portion of the protruding part of the single-radiopaque component may have a thickness greater than a thickness of a central portion of the protruding part.

Optionally, in the stent, the upper surface may be a convex or concave surface.

Optionally, in the stent, the embedded part of the single-radiopaque component may include a side surface coming into contact with the receptacle, the side surface being parallel to the axis, and wherein before the single-radiopaque component is received in the receptacle, the lower surface is oriented at an angle of smaller than 90 degrees relative to the side surface.

Optionally, in the stent, the protruding part of the single-radiopaque component may have a diameter greater than or equal to 300 µm and smaller than or equal to 500 µm.

Optionally, in the stent, the receptacle may be defined in a strut at one or each of the proximal end and distal end of the stent body, and wherein the protruding part of the single-radiopaque component has a maximum outer diameter greater than or equal to a length of the strut.

Optionally, in the stent, the protruding part of the single-radiopaque component may have an edge pressed against a surface of the stent body.

Optionally, in the stent, the protruding part of the single-radiopaque component may have an edge portion bending along a surface of the stent body.

Optionally, in the stent, the protruding part may have a thickness of from 20 µm to 60 µm.

Optionally, in the stent, the protruding part may be situated inside or outside the stent body.

The present invention provides another stent, including a stent body and a single-radiopaque component disposed at one or each of a proximal end and a distal end of the stent body, the stent body composed of rings and struts, the single-radiopaque component formed of a metal wire wound on one of the struts.

Optionally, in the stent, the strut may form an annulus structure, the single-radiopaque component formed of the metal wire wound on the annulus structure.

Optionally, in the stent, the annulus structure may have a polygonal shape, a circular shape, an "8" shape, an elliptical shape or a combination of one or more thereof.

Optionally, in the stent, the metal wire may have a diameter of from 20 µm to 60 µm.

In summary, the present invention provides a stent including a stent body and a single-radiopaque component disposed at one or each of a proximal end and a distal end of the stent body. The stent body is composed of rings and struts, the single-radiopaque component has an embedded part received in a receptacle of the stent body and a protruding part protruding out of a surface of the stent body. An area of the protruding part of the single-radiopaque component is larger than an area of the embedded part, allowing the single-radiopaque component to appear wider and thicker in a radiologic image, enhancing radiopacity of the stent during surgery.

Additionally, before the single-radiopaque component is received in the receptacle, a lower surface of the protruding part may be oriented at an angle of smaller than 90 degrees with respect to a side surface of the embedded part. In this way, after the single-radiopaque component is fitted into the receptacle, the lower surface can be tightly pressed against the stent body, reducing the risk of warpage or deformation of the protruding part.

Further, the single-radiopaque component may be made up of a metal wire, which allows tight adhesion of the single-radiopaque component to the stent, without detachment therebetween under stress arising from the expansion of the stent.

BRIEF DESCRIPTION OF THE DRAWINGS

FIG. 1b is a top view of FIG. 1a.

FIG. 2b is a top view of FIG. 2a.

FIG. 3b is a top view of FIG. 3a.

FIG. 4b is a top view of FIG. 4a.

FIG. 5b is a top view of FIG. 5a.

FIG. 6b is a top view of FIG. 6a.

FIG. 7b is a top view of FIG. 7a.

FIG. 8b is a top view of FIG. 8a.

FIG. 9b is a top view of FIG. 9a.

FIG. 13 is a schematic partial view of a stent according to a sixth embodiment of the present invention.

FIG. 14 is a schematic partial view of each of the stent bodies according to the first, second, third, fourth, fifth and sixth embodiments.

FIG. 15 is a diagram illustrating radiopacity of the stent according to the fourth embodiment.

In these figures, 1-single-radiopaque component; 10-embedded part; 100-side surface; 11-protruding part; 110-upper surface; 111-lower surface; 2-stent body; 3-receptacle; 4-annulus structure; 5-metal wire.

DETAILED DESCRIPTION

Stents proposed in the present invention will be described in greater detail below with reference to specific embodiments which are to be read in conjunction with the accompanying drawings. Features and advantages of the invention will be more readily apparent from the following detailed description, and from the appended claims. Note that the figures are provided in a very simplified form not necessarily presented to scale, with the only intention of facilitating convenience and clarity in explaining the embodiments.

FIG. 14 schematically illustrates part of a stent body according to the present invention. As shown, the stent body 2 is composed of rings and struts. Strut(s) at one or each of a proximal end and a distal end of the stent body each defines a receptacle 3 for receiving a single radiopaque component (not shown in the figure). The receptacle 3 extends substantially perpendicularly to a direction in which the strut extends, so that the single-radiopaque component extends in the receptacle 3 in essence radially with respect to the stent body 2.

According to the present invention, in order for increased stent radiopacity to be achieved, the single-radiopaque component is structurally designed to be partially received in the receptacle in the stent body (this part is referred hereinafter as an "embedded part") and partially protrude out of the surface of the stent body (referred hereinafter as a "protruding part"). The area of the protruding part of the single-radiopaque component is larger than the area of the embedded part, wherein the area refers to the projected area when viewed radially with respect to the stent body 2, thereby significantly increasing the radiopaque area and thickness of the single-radiopaque component. This leads to improved radiopacity during the procedure of the stent. As this is achieved without employing any additional radiopaque marker or a longer strut, degradation of stent performance is avoided. The present invention will be described in greater detail below with reference to a few specific embodiments so that a better understanding thereof can be obtained.

Embodiment 1

Figure 4A:
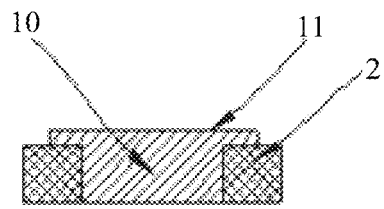
FIG. 4a is a schematic cross-sectional view of a further single-radiopaque component received in the receptacle in the stent body according to the first embodiment of the present invention.
Figure 4B:
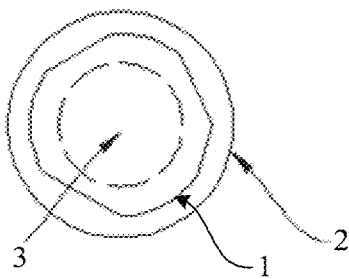

According to this first embodiment, examples of the single-radiopaque component received in the receptacle of the stent body are shown in FIGS. 1a to 4b. As shown in FIGS. 1a, 2a, 3a and 4a, the single-radiopaque component 1 has a similar T-shaped longitudinal cross-section in the illustrated cases. More specifically, in these examples, in terms of longitudinal cross-section, the embedded part 10 of the single-radiopaque component 1 remains constant, while the protruding part 11 of the single-radiopaque component 1 varies from case to case. The transverse and longitudinal cross-sections of the protruding part 11 will be described by way of example. For example, as shown in FIGS. 1b and 2b, the protruding part 11 may have a circular transverse cross-section. As shown in FIG. 3b, the protruding part 11 may alternatively have a hexagonal transverse cross-section. Possible transverse cross-sections of the protruding part 11 are not limited to these circular and hexagonal shapes, because they may also include other shapes, such as an irregular shape as shown in FIG. 4b, as long as the area of the protruding part 11 is larger than the area of the embedded part 10.

Preferably, the single-radiopaque component 1 may be made of a high-density metallic material such as gold or platinum. And the longitudinal cross-section of the single-radiopaque component 1 may alternatively be ram's-horn-shaped without being limited to a T-like shape.

With continued reference to FIGS. 1a, 2a, 3a and 4a, the embedded part 10 of the single-radiopaque component 1 is received within the receptacle 3, while the protruding part 11 protrudes out of the receptacle 3. The protruding part 11 may be located inside or outside the stent body 2 in a radial direction of the stent body 2. The protruding part 11 may have a linear longitudinal cross-section and cover at least part of the stent body 2 around the receptacle 3 so that it does not widen the covered part of the stent body 2 and thus will not affect the compressive properties of the stent. According to this embodiment, the stent can offer good radiopacity during a procedure in which the stent is employed.

Figure 1A:
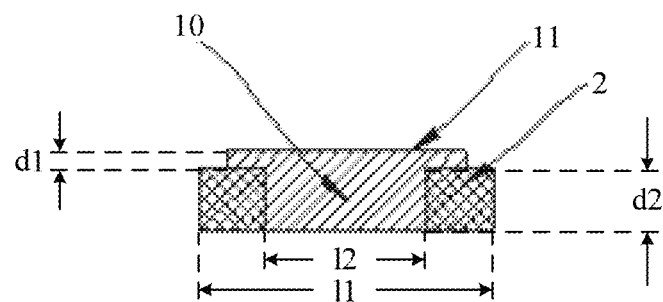
FIG. 1a is a schematic cross-sectional view of a single-radiopaque component received in a receptacle in a stent body according to a first embodiment of the present invention.
Figure 1B:
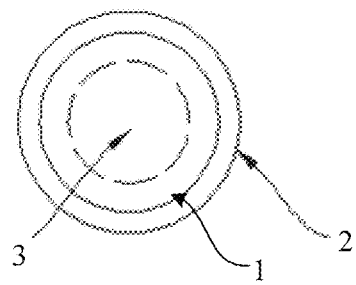
Figure 2A:
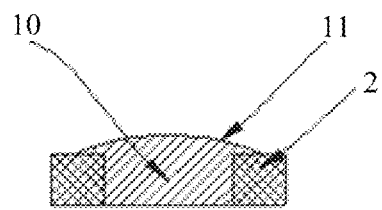
FIG. 2a is a schematic cross-sectional view of another single-radiopaque component received in the receptacle in the stent body according to the first embodiment of the present invention.
Figure 2B:
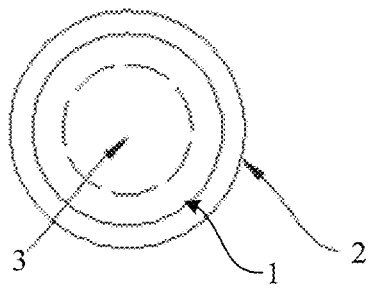
Figure 3A:
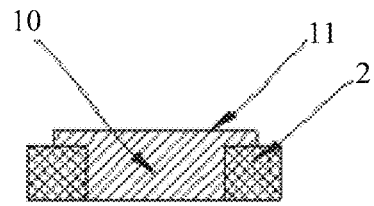
FIG. 3a is a schematic cross-sectional view of a further single-radiopaque component received in the receptacle in the stent body according to the first embodiment of the present invention.
Figure 3B:
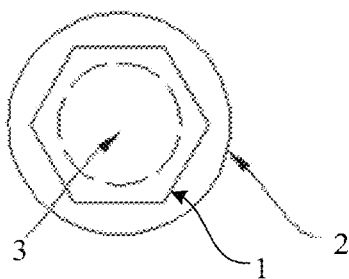

In order to ensure good radiopacity and fitness, for example, as shown in FIG. 1a, the protruding part 11 may have a thickness d1 ranging from 20 µm to 60 µm, and the embedded part 10 may have a thickness d2 that is smaller than or equal to a wall thickness of the stent body 2. In a direction perpendicular to the wall thickness of the stent body 2, the protruding part 11 may extend a length 11 ranging from 200 µm to 600 µm. In a direction perpendicular to the wall thickness of the stent body 2, the embedded part 10 may extend a length 12 ranging from 200 µm to 500 µm. In the case of FIG. 2a, the thickness dl of the protruding part 11 is meant to refer to the maximum thickness of the protruding part 11 outside the stent body 2.

Embodiment 2

The embodiment 2 provides a further stent. As shown in FIGS. 5a to 6b, this second embodiment differs from Embodiment 1 in that two single-radiopaque components 1 are received in each receptacle 3 of the stent. With this design, an increased thickness of the radiopaque material can be achieved at the same location(s) of the stent, leading to significantly improved radiopacity.

Figure 5A:
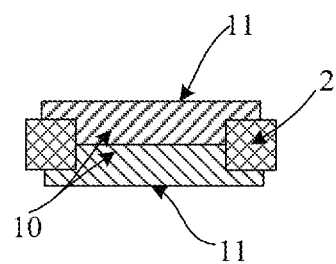
FIG. 5a is a schematic cross-sectional view of single-radiopaque components received in a receptacle in a stent body according to a second embodiment of the present invention.
Figure 5B:
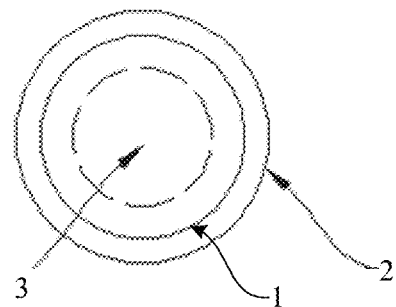
Figure 6A:
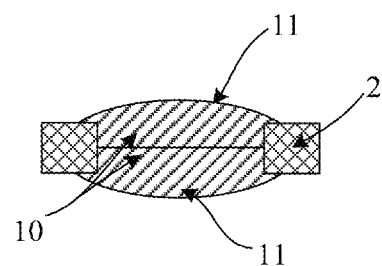
FIG. 6a is a schematic cross-sectional view of other single-radiopaque components received in the receptacle in the stent body according to the second embodiment of the present invention.
Figure 6B:
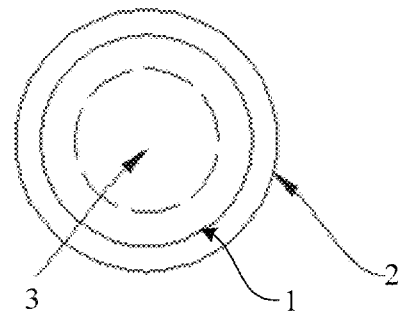

Referring to FIGS. 5a and 6a, the number of the receptacle 3 is one and the number of the single-radiopaque components 1 is two. The embedded parts 10 of two single-radiopaque components 1 are respectively received within the receptacle 3. Preferably, the two embedded parts 10 may be joined or riveted together and may be made of the same or different materials. In the radial direction of the stent body 2, one of the two protruding parts 11 of one single-radiopaque component 1 is located inside the stent body 2, another one of the two protruding parts 11 of another single-radiopaque component 1 is located outside the stent body 2. The two single-radiopaque components 1 may constitute a single radiopaque block. Reference can be made to the description of Embodiment 1 for details in the shapes of the protruding parts 11, and a detailed description thereof is deemed unnecessary and is therefore omitted here.

In order to ensure good radiopacity and fitness, the protruding part 11 of each of the single-radiopaque components 1 may have a thickness ranging from 20 µm to 60 µm, and a total thickness of the embedded parts 10 of the single-radiopaque components 1 may be smaller than or equal to the wall thickness of the stent body 2. For each of the single-radiopaque components 1, the protruding part 11 may extend a length ranging from 200 µm to 600 µm, while the embedded part 10 may extend a length ranging from 200 µm to 500 µm, in a direction perpendicular to the wall thickness of the stent body 2.

Embodiment 3

The embodiment 3 provides a further stent. As shown in FIGS. 7a to 9b, this third embodiment differs from Embodiment 1 in that the protruding part 11 of the single-radiopaque component 1 received in each receptacle 3 of the stent has a different structure. In order for increased radiopacity to be achieved with guaranteed secure connection between the single-radiopaque component 1 and the stent body 2, the protruding part of the single-radiopaque component has an edge portion bending along the surface of the stent body.

Figure 7A:
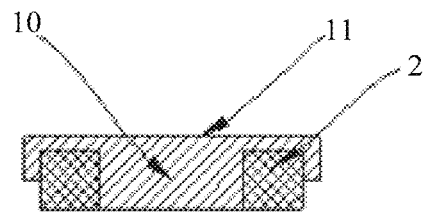
FIG. 7a is a schematic cross-sectional view of a single-radiopaque component received in a receptacle in a stent body according to a third embodiment of the present invention.
Figure 7B:
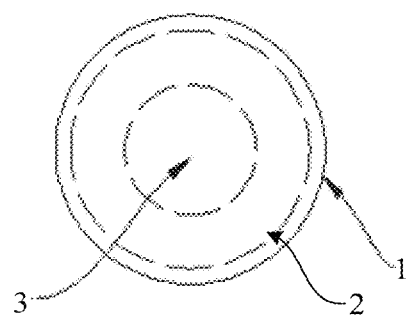
Figure 8A:
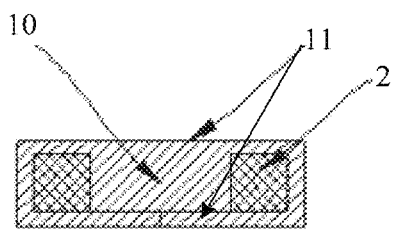
FIG. 8a is a schematic cross-sectional view of another single-radiopaque component received in the receptacle in the stent body according to the third embodiment of the present invention.
Figure 8B:
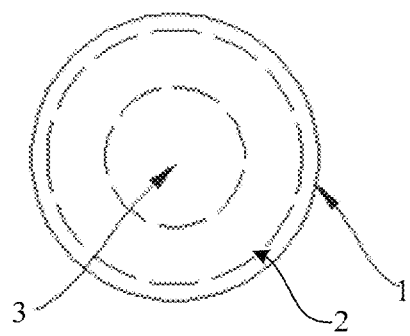

Preferably, for example, as shown in FIG. 7a, the protruding part 11 may have an inverted U-shaped longitudinal cross-section. In other words, the edge portion is adjacent to the part of the stent body 2 around the receptacle 3. Alternatively, as shown in FIG. 8a, the protruding part 11 may have a closed circular longitudinal cross-section. In this case, the protruding part 11 completely wraps the part of the stent body 2 around the receptacle 3. Reference can be made to the description of Embodiment 1 for details in the transverse cross-section of the protruding part 11, and a detailed description thereof is deemed unnecessary and is therefore omitted here.

Figure 9A:
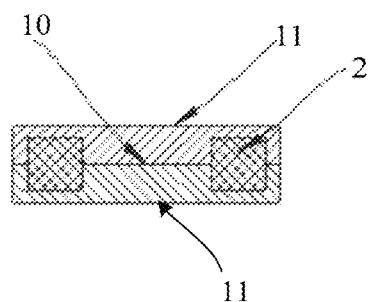
FIG. 9a is a schematic cross-sectional view of a further single-radiopaque component received in the receptacle in the stent body according to the third embodiment of the present invention.
Figure 9B:
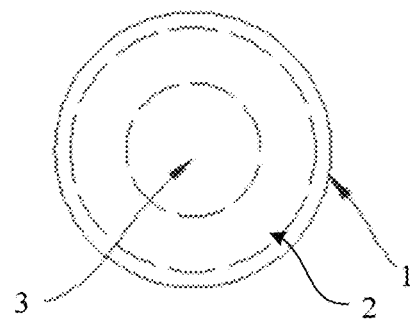

Referring to FIG. 9a, two structures, as shown in FIG. 7a, may be received in the receptacle 3, thus resulting in a greater overall thickness of the radiopaque material and hence better radiopacity while ensuring stronger connection between the single-radiopaque components 1 and the stent body 2.

In order to ensure good radiopacity and fitness, the protruding part 11 may have a thickness ranging from 20 µm to 60 µm, while the embedded part 10 may have a thickness smaller than or equal to the wall thickness of the stent body 2. In a direction perpendicular to the wall thickness of the stent body 2, the protruding part 11 may extend a length ranging from 200 µm to 600 µm. In a direction perpendicular to the wall thickness of the stent body 2, the embedded part 10 may extend a length ranging from 200 µm to 500 µm.

Embodiment 4

Figure 10:
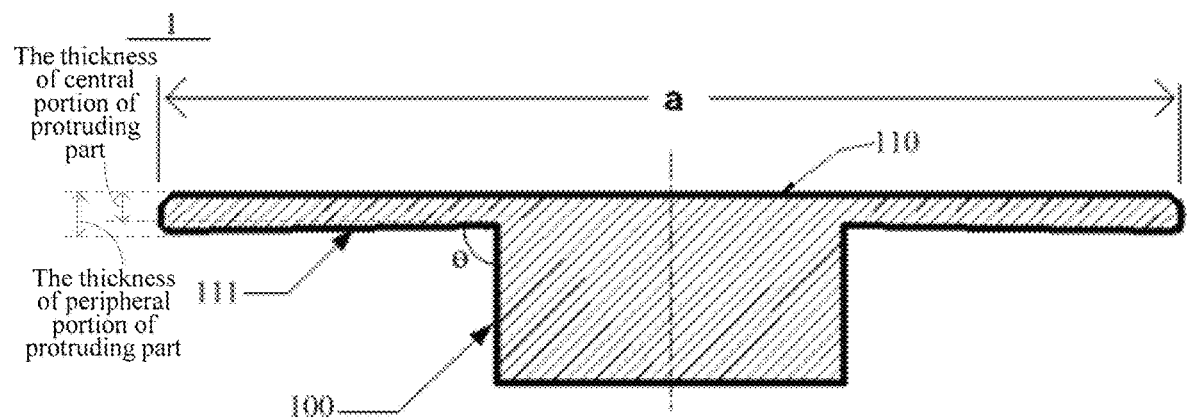
FIG. 10 is a schematic cross-sectional view of a single-radiopaque component according to a fourth embodiment of the present invention.
Figure 11:
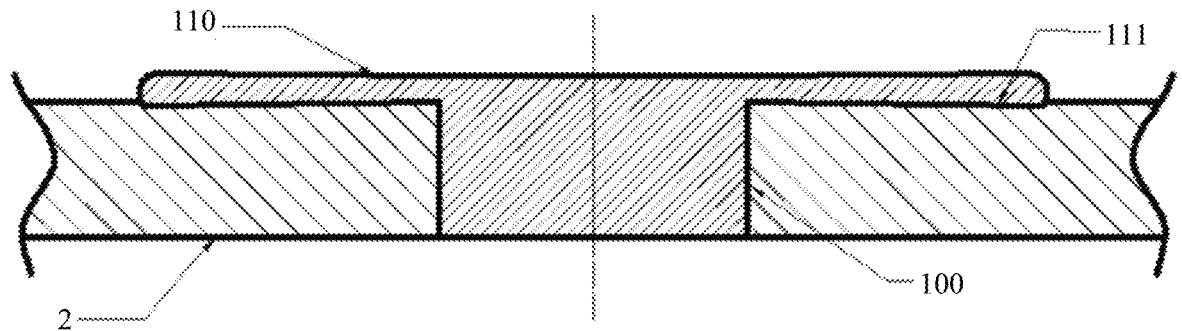
FIG. 11 is a schematic cross-sectional view of the single-radiopaque component received in a receptacle in a stent body according to the fourth embodiment of the present invention.
Figure 16:
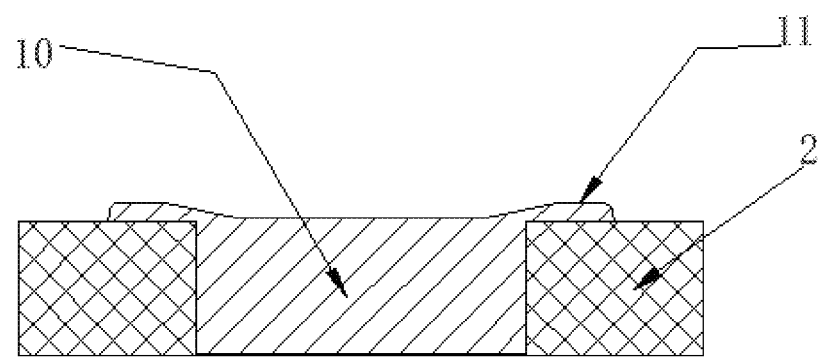
FIG. 16 is a schematic partial of the upper surface of the protruding part being concave.

Referring to FIGS. 10 and 11, according to this fourth embodiment, the protruding part of each single-radiopaque component in the stent has a central portion and a peripheral portion thicker than the central portion (i.e., being thinner in the center and thicker in the periphery). The protruding part 11 of each single-radiopaque component 1 may have an upper surface 110 and a lower surface 111. The upper surface 110 may cross an axis of the single-radiopaque component at an angle of greater than 90 degrees or smaller than 90 degrees. The upper surface 110 may be either convex or concave (as shown in FIG. 16). The embedded part 10 of the single-radiopaque component 1 may have a side surface 100 come into contact with an inner side wall of the receptacle. The side surface 100 is parallel to the axis.

According to this embodiment, the protruding part of the single-radiopaque component may have a diameter a preferred to lie between 300 µm and 500 µm, with 410 µm and 460 µm being more preferred. As shown in FIG. 15, FIG. 15 is a schematic illustration of radiopacity results of several DSA (digital subtraction angiography) test cycles. The images were obtained at 15 fps (frames per second) in a cinema mode, with black dots therein indicating radiopaque markers. As can be seen from FIG. 15, a radiopaque marker with a protruding part having a diameter of 375 µm according to the present invention exhibits better radiopacity than a conventional radiopaque marker pair (indicated at "Similar Product" in the figure), and a radiopaque marker with a protruding part having a diameter of 410 µm according to the present invention exhibits even better radiopacity than the 375-µm one.

The single-radiopaque component according to this embodiment is structurally designed to lower the risk of warpage or deformation of the protruding part during the use of the single-radiopaque component by enhancing the adhesion between the protruding part and the stent body.

More specifically, as shown in FIG. 10, prior to the disposal of the single-radiopaque component in the receptacle, the angle θ between the lower surface 111 of the protruding part and the side surface 100 of the embedded part 10 may be designed to be smaller than 90 degrees. Additionally, the protruding part of the single-radiopaque component may be designed to have the aforementioned shape with a central portion and a peripheral portion thicker than the central portion (i.e., thinner in the center and thicker in the periphery). When the single-radiopaque component is pressed into the receptacle, it may experience a deformation leading to an angle between the upper surface 110 and its axis of smaller than 90 degrees and an increase in the angle θ between the lower surface 111 and the side surface 100, compared to the shape before the single-radiopaque component is fitted into the receptacle. In this way, the lower surface 111 can tightly abut against the surface of the stent body and thereby reduce the risk of warpage or deformation of the protruding part. In addition, since the protruding part of the single-radiopaque component is thinner in the center and thicker in the periphery, the edge of the protruding part will be forced slightly into the material of the stent body. This can additionally reduce the risk of warpage or deformation of the protruding part.

Compared to the conventional radiopaque marker pair, use of the single-radiopaque component according to this embodiment can further result in savings in the used platinum material, thus allowing the stent to be sold at a lower unit price.

Embodiment 5

Figure 12:
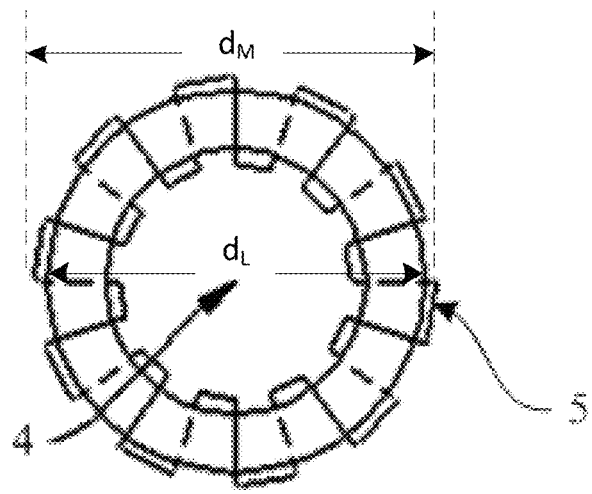
FIG. 12 is a schematic partial view of a stent according to a fifth embodiment of the present invention.

Referring to FIG. 12, a stent according to this fifth embodiment includes a stent body and single-radiopaque component(s) disposed at a proximal and/or a distal end of the stent body. The stent body is composed of rings and struts, and each of the single-radiopaque component(s) is made up of a metal wire 5 wound on one of the struts and has a protruding part with a maximum outer diameter $d_M$ greater than or equal to a length $d_L$ of the strut. The metal wire 5 may be, but is not limited to, a gold wire or platinum wire.

More specifically, the strut may form an annulus structure 4 on which the metal wire 5 acting as the single-radiopaque component is wound. Therefore, the metal wire has a general shape consistent with a shape of the annulus structure 4, which is, for example, a trapezoid, an arc, a square or an irregular shape.

Figure 17:
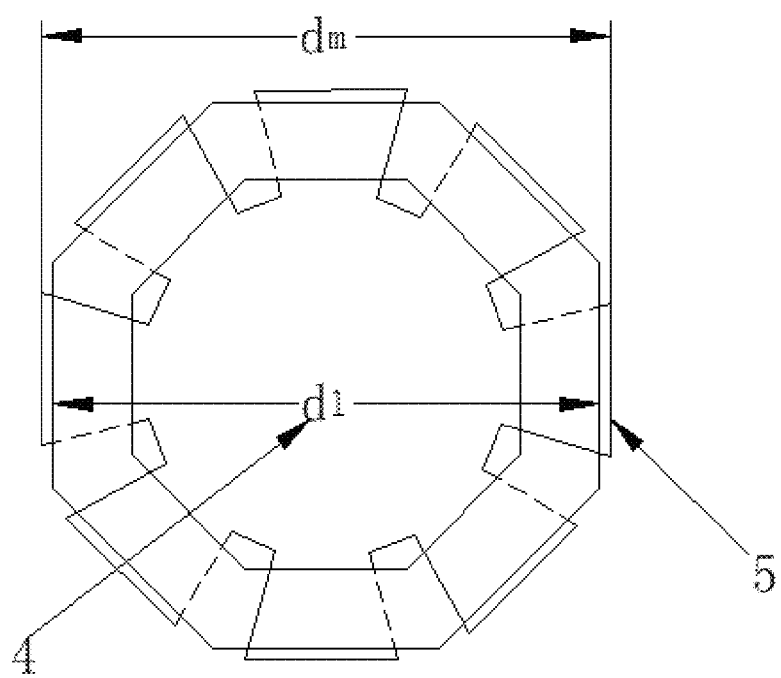
FIG. 17 is a schematic partial view of an annulus structure having a polygonal shape.
Figure 18:
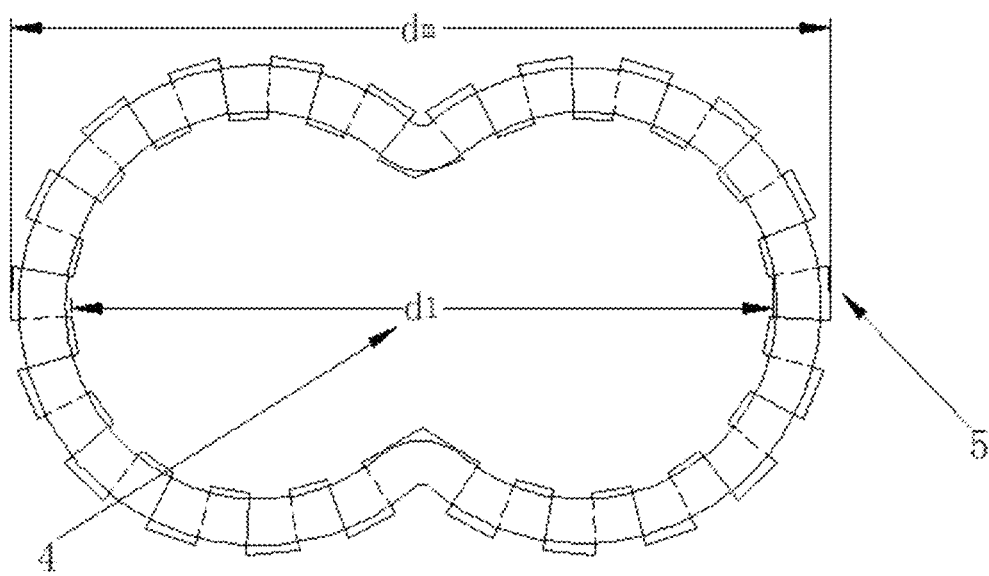
FIG. 18 is a schematic partial view of an annulus structure having an "8" shape.

The annulus structure 4 may have a polygonal shape (as shown in FIG. 17), a circular shape, an "8" shape ( as shown in FIG. 18), an elliptical shape or a combination of one or more thereof. In order to ensure good radiopacity and fitness of the single-radiopaque component, the metal wire may have a diameter ranging from 20 µm to 60 µm.

According to this embodiment, winding the metal wire allows tight adhesion of the single-radiopaque component to the stent, without detachment therebetween under stress arising from the expansion of the stent.

Embodiment 6

The embodiment 6 provides a further stent. As shown in FIG. 13, this sixth embodiment differs from Embodiment 5 in that each single-radiopaque component is designed to have a maximum outer diameter $d_M$ of the protruding part that is greater than or equal to a length $d_L$ of the strut. The single-radiopaque component may be a high-density metallic material, such as gold or platinum, coated on the strut. In this way, the single-radiopaque component is a generally structure having two end parts protruding beyond the strut (i.e., the protruding part) and a central part received in the receptacle (i.e., the embedded part) which may be either integrated or joined with the protruding part. The embedded part may have a circular or polygonal transverse cross-section. Compared to other Embodiments, this embodiment allows an increased length of the single-radiopaque component so that it may be more easily identified by the operator.

In order to ensure good radiopacity and fitness of the single-radiopaque component, the protruding part may have a thickness in the range of 20 µm-60 µm and a width close to a width of the strut, while the embedded part may have a thickness smaller than or equal to a thickness of the stent body.

It is noted that the embodiments disclosed herein are described in a progressive manner, with the description of each embodiment focusing on its differences from other embodiments. Reference can be made between the embodiments for their identical or similar parts.

To sum up, the present invention provides a stent including a stent body and single-radiopaque component disposed at one or each of a proximal end and a distal end. The stent body is composed of rings and struts, and each of the single-radiopaque component(s) has an embedded part received in a receptacle of the stent body and a protruding part protruding out of a surface of the stent body. The area of the protruding part of the single-radiopaque component(s) is larger than an area of the embedded part and thus allows the single-radiopaque component to appear wider and thicker in a radiologic image, enhancing radiopacity of the stent during surgery.

Additionally, before the single-radiopaque component is received in the receptacle, a lower surface of the protruding part may be oriented at an angle of smaller than 90 degrees with respect to a side surface of the embedded part. In this way, after the single-radiopaque component is fitted into the receptacle, the lower surface can be tightly pressed against the stent body, reducing the risk of warpage or deformation of the protruding part.

Further, the single-radiopaque component may be made up of a wound metal wire, which allows tight adhesion of the single-radiopaque component to the stent, without detachment therebetween under stress arising from the expansion of the stent.

The description presented above is merely that of a few preferred embodiments of the present invention without limiting the scope thereof in any sense. Any and all changes and modifications made by those of ordinary skill in the art based on the above teachings fall within the scope as defined in the appended claims.

What is claimed is:

1. A stent, comprising a stent body and a single-radiopaque component disposed at one or each of a proximal end and a distal end of the stent body, the stent body composed of rings and struts, the single-radiopaque component formed of a metal wire wound on one of the struts, wherein the strut forms an annulus structure, the single-radiopaque component formed of the metal wire wound on the annulus structure.

2. The stent according to claim 1, wherein the annulus structure has a polygonal shape, a circular shape, an "8" shape, an elliptical shape or a combination of one or more thereof.

3. The stent according to claim 1, wherein the metal wire has a diameter of from 20 μm to 60 μm.

* * * * *